(12) United States Patent
Suh et al.

(10) Patent No.: US 8,889,749 B2
(45) Date of Patent: Nov. 18, 2014

(54) PREPARATION METHOD OF HYDROPHOBIC MONOLITH TYPE SILICA AEROGEL

(71) Applicant: Korea Institute of Science and Technology, Seoul (KR)

(72) Inventors: Dong Jin Suh, Seoul (KR); Gi Seok Yang, Seoul (KR); Jae Wook Choi, Incheon (KR); Young Hyun Yoon, Seoul (KR); Yun Su Lee, Chungcheongnam-do (KR); Jeong Myeong Ha, Seoul (KR)

(73) Assignee: Korea Institute of Science and Technology, Seoul (KR)

( * ) Notice: Subject to any disclaimer, the term of this patent is extended or adjusted under 35 U.S.C. 154(b) by 15 days.

(21) Appl. No.: 13/684,282

(22) Filed: Nov. 23, 2012

(65) Prior Publication Data

US 2013/0296596 A1     Nov. 7, 2013

(30) Foreign Application Priority Data

May 4, 2012   (KR) .................... 10-2012-0047484

(51) Int. Cl.
  *C08J 9/236*   (2006.01)
  *C07F 7/18*    (2006.01)

(52) U.S. Cl.
  CPC ..................... *C07F 7/188* (2013.01)
  USPC .................. 521/57; 521/53; 521/64

(58) Field of Classification Search
  USPC ............... 521/53, 57, 64; 556/457, 462, 470
  See application file for complete search history.

(56) References Cited

U.S. PATENT DOCUMENTS

| 5,830,387 A * | 11/1998 | Yokogawa et al. ............. 252/62 |
| 5,888,425 A | 3/1999 | Schwertfeger et al. |
| 2009/0247655 A1 * | 10/2009 | Kim et al. ...................... 521/64 |

FOREIGN PATENT DOCUMENTS

| JP | 05-279011 A | 10/1993 |
| JP | 2725573 B2 | 3/1998 |
| JP | 2000-264620 A | 9/2000 |
| KR | 19990009158 A | 2/1999 |
| KR | 1020110125773 A | 11/2011 |
| WO | 98/02336 A1 | 1/1998 |

OTHER PUBLICATIONS

C.J. Brinker, et al; "Sol-Gel Processing", Book Sol-Gel Science Chapter 1: Introduction Academic Press, New York, Published © 1990, 4 pages.

* cited by examiner

*Primary Examiner* — Sudhakar Katakam
*Assistant Examiner* — Pancham Bakshi
(74) *Attorney, Agent, or Firm* — Ladas & Parry LLP

(57) ABSTRACT

Provided is a method for preparing hydrophobic monolithic silica aerogel, comprising dipping monolithic wet silica gel obtained by using an alkoxide precursor into an alkylsilane solution as a dipping solution to perform hydrophobitization of the surface and inner part of the monolithic wet silica gel by a dipping process. The method is economical by virtue of the use of a small amount of alkylsilane compound and imparts hydrophobic property to monolithic silica aerogel simply in a cost efficient and time efficient manner. In addition, the method reduces shrinkage of hydrophobic monolithic silica aerogel, enables production of hydrophobic monolithic silica aerogel in a translucent form, and allows the hydrophobic monolithic silica aerogel to maintain low heat conductivity similar to the heat conductivity of hydrophilic silica aerogel. The hydrophobic monolithic silica aerogel may be used directly as a heat insulating panel by virtue of excellent hydrophobic property and heat insulating property.

4 Claims, 2 Drawing Sheets

PREPARATION METHOD OF HYDROPHOBIC MONOLITH TYPE SILICA AEROGEL

CROSS-REFERENCE TO RELATED APPLICATION

This application claims priority to Korean Patent Application No. 2012-0047484, filed on May 4, 2012, and all the benefits accruing therefrom under 35 U.S.C. §119, the contents of which in its entirety are herein incorporated by reference.

BACKGROUND

1. Field

The present disclosure relates to a method for preparing monolithic silica aerogel. More particularly, the present disclosure relates to a method for preparing monolithic silica aerogel, including hydrophobitizing monolithic wet silica gel by dipping it into an alkylsilane solution.

2. Description of the Related Art

Silica aerogel, which is given many attentions recently as an ultralight advanced material, is a material having unlimited applicability to industrial fields of energy and environment by virtue of its physical properties, such as high porosity, large surface area, low density, transparency and low heat conductivity. Therefore, porous silica aerogel is applicable to industrial fields related to heat insulating materials, noise-protecting materials, storage materials, ultralight materials for cars and space crafts, electrochemical materials, catalysts of electronic materials, catalyst carriers, or the like. Thus, it is expected that silica aerogel is useful as a key material in various industrial fields.

Particularly, use of silica aerogel as a heat insulating material is one of the most commercially practical uses of silica aerogel. Transparent silica aerogel may be used as a heat insulating window, while opaque silica aerogel may be used effectively as a heat insulating material for various low-temperature or high-temperature heat insulating materials. Transparent aerogel allows transmission of solar light and effective shielding of heat, and thus may provide an energy-saving window system when used for a skylight. Currently, skylight ceiling window systems having a double pane window in which translucent silica aerogel particles are filled have been commercialized and distributed for practical use. However, such systems have a limitation in transparency and are problematic in that the aerogel particles are driven downwardly due to the gravity during long-time use. Meanwhile, monolithic transparent aerogel may be filled into double pane windows to be used as heat insulating windows. However, except some specialized uses, it is difficult to commercialize such windows in terms of cost efficiency, because silica aerogels are required to be formed into monoliths having the same size as the windows.

Monolithic hydrophilic silica aerogel shows transparency and high heat insulating property, but is sensitive to moisture in the air. Thus, such silica aerogel causes cracking on the surface and inner part of the aerogel when exposed to the air for a long time, thereby making it difficult to maintain its originally high heat insulating property. Therefore, it is required to provide a method for preventing moisture absorption in the atmosphere for the purpose of commercialization of such aerogel. For this, many studies have been conducted and many methods have been suggested to provide hydrophobic aerogel.

Particularly, the following methods for preparing hydrophobic silica aerogel have been suggested. First, Korean Patent Laid-Open publication No. 2011-0125773 discloses a method for preparing hydrophobic silica aerogel, which includes preparing a sol solution by using a tetraethoxysilane precursor and an alcohol solvent, and introducing hexamethyldisilazane during the synthesis of gel. This is a general method for imparting hydrophobic property to silica aerogel. However, the method results in a rapid increase in shrinkage of silica aerogel and degradation of heat conductivity.

Next, U.S. Pat. No. 5,888,425 discloses a method for preparing hydrophobic silica aerogel, which includes preparing silicatic lyogel, subjecting the lyogel to a solvent exchange with another organic solvent, reacting the gel with a chlorine-free silylating agent to hydrophobitize it via alkyl radical reaction, and subjecting the resultant gel to subcritical drying. WO 98/02336 discloses a method for preparing hydrophobic silica aerogel, which includes reacting water glass with acid to form lyogel, subjecting the lyogel to a solvent exchange with another organic solvent, silylating the gel by using disiloxane, and subjecting the resultant gel to drying. As such, the above methods essentially require a solvent exchange with an organic solvent and use of an excessive amount of silylating agent for hydrophobitization, and thus have poor cost efficiency.

In addition, the process of hydrophobitization in the methods for preparing hydrophobic silica aerogel according to the related art has a difficulty in application to monolithic aerogel, is complicated due to the use of mixed solution after pH adjustment, and shows poor cost efficiency due to the continuous use of expensive butanol and alkylsilylating agent from a reflux process to a hydrophobitization operation. Further, the drying operation at high temperature after the hydrophobitization causes problems of high shrinkage and degradation of heat conductivity.

To enhance the applicability of hydrophobic monolithic silica aerogel, it is important to provide aerogel to which hydrophobic property is imparted while minimizing deformation of aerogel. According to the related art, silica aerogel is hydrophobitized by using an excessive amount of silylating agent. Thus, the related art is not cost efficient and is problematic in that it causes an increase in shrinkage and degradation of heat insulating property during the hydrophobitization. Under these circumstances, there is a need for providing hydrophobic monolithic silica aerogel having excellent heat insulating property by imparting hydrophobic property thereto in a more cost-efficient manner.

REFERENCES OF THE RELATED ART

Patent Document

Korean Laid-Open Patent Publication No. 2011-0125773
U.S. Pat. No. 5,888,425
WO 98/02336

SUMMARY

The present disclosure is directed to providing a method for preparing hydrophobic monolithic silica aerogel having excellent hydrophobic property and heat insulating property in a simple and cost efficient manner, which comprises carrying out hydrophobitization through a dipping process by dipping monolithic wet silica gel obtained by using an alkoxide precursor into an alkylsilane solution as a dipping solution. The present disclosure is also directed to providing a method for controlling a degree of hydrophobitization of hydrophobic monolithic silica aerogel.

In one aspect, there is provided a method for preparing hydrophobic monolithic silica aerogel, comprising: dipping monolithic wet silica gel obtained by using an alkoxide precursor into an alkylsilane solution as a dipping solution to perform hydrophobitization of the surface and inner part of the monolithic wet silica gel by a dipping process.

According to an embodiment, the method may comprise: preparing monolithic wet silica gel by using an alkoxide precursor; hydrophobitizing the monolithic wet silica gel by dipping the wet gel into an alkylsilane solution through a dipping process; and carrying out supercritical drying of the hydrophobitized monolithic wet silica gel.

According to an embodiment, the alkylsilane may be at least one selected from the group consisting of methyltrimethoxysilane, ethyltrimethoxysilane, propyltrimethoxysilane, phenyltrimethoxysilane, hexamethyldisilane, methoxytrimethylsilane, triethylethoxysilane, trimethylchlorosilane, vinyltriethoxysilane and dimethyldiethoxysilane.

According to an embodiment, the solvent used for the alkylsilane solution may be selected from the group consisting of methanol, dimethylformamide and a mixture thereof.

According to an embodiment, the alkylsilane solution may have a concentration of 3-30 vol %.

According to an embodiment, the alkylsilane solution may be maintained at a temperature of 25-80° C.

According to an embodiment, the monolithic wet silica gel may be dipped in the alkylsilane solution for 6-48 hours.

The method for preparing hydrophobic monolithic silica aerogel disclosed herein is economical by virtue of the use of a small amount of alkylsilane compound and imparts hydrophobic property to monolithic silica aerogel in a cost efficient and time efficient manner. In addition, the method disclosed herein reduces shrinkage of hydrophobic monolithic silica aerogel, enables production of hydrophobic monolithic silica aerogel in a translucent form, and allows the hydrophobic monolithic silica aerogel to maintain low heat conductivity similar to the heat conductivity of hydrophilic silica aerogel. Further, the hydrophobic monolithic silica aerogel may be used directly as a heat insulating panel by virtue of excellent hydrophobic property and heat insulating property.

DETAILED DESCRIPTION

Figure 1:
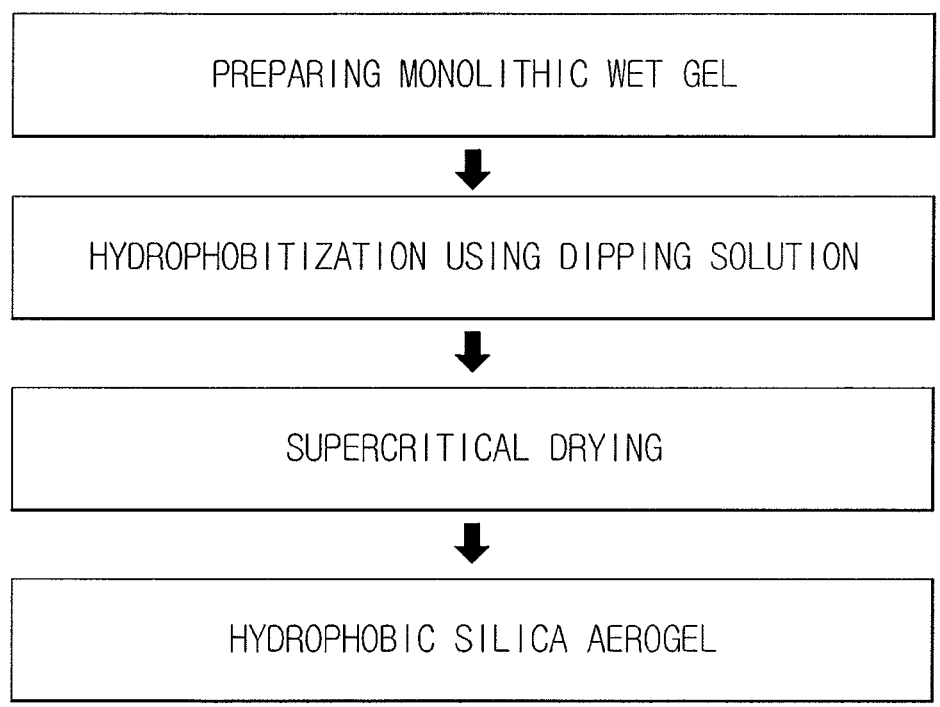
FIG. 1 is a flow chart of the method for preparing hydrophobic monolithic silica aerogel according to an embodiment.
Figure 2:
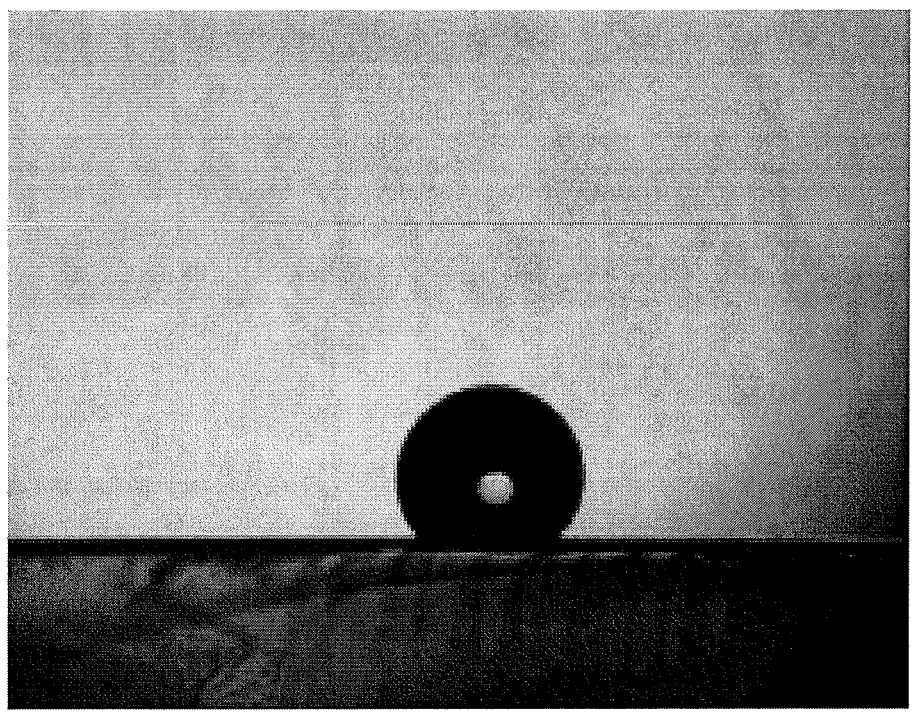
FIG. 2 is a photograph illustrating a method for measuring water contact angles of hydrophobic monolithic silica aerogel according to an embodiment.

Exemplary embodiments now will be described more fully hereinafter with reference to the accompanying drawings, in which exemplary embodiments are shown.

Provided is a method for preparing hydrophobic monolithic silica aerogel, comprising dipping monolithic wet silica gel obtained by using an alkoxide precursor into an alkylsilane solution as a dipping solution to perform hydrophobitization of the surface and inner part of the monolith wet silica gel.

More particularly, the method disclosed herein comprises: preparing monolithic wet silica gel by using an alkoxide precursor; dipping the monolithic wet silica gel into an alkylsilane solution to perform hydrophobitization of the monolithic wet silica gel by a dipping process; and carrying out supercritical drying of the hydrophobitized monolithic wet silica gel.

Hereinafter, the method for preparing hydrophobic monolithic silica aerogel will be explained in more detail.

First, monolithic wet silica gel is prepared by using an alkoxide precursor.

The alkoxide precursor may be at least one selected from a tetramethoxysilane precursor and tetraethoxysilane precursor, but is not limited thereto.

Herein, the monolithic wet silica gel may be prepared by any method known to those skilled in the art. For example, it may be prepared by a known sol-gel process, but is not limited thereto. Particularly, to provide monolithic wet silica gel, a gelation catalyst is introduced to a silica sol solution, followed by mixing for a predetermined time, and introducing the solution to a mold with a predetermined size while maintaining its solution state, thereby carrying out gelation. The sol-gel process is described in many references including Sol-Gel Science, C. J. Brinker and G. W. Scherer, New York, Academic press, 1990.

The wet silica gel has a surface with a Si—OH structure.

Then, the monolithic wet silica gel is dipped into an alkylsilane solution so that the wet gel is hydrophobitized through a dipping process.

Although there is no particular limitation, the alkylsilane may be at least one selected from the group consisting of methyltrimethoxysilane, ethyltrimethoxysilane, propyltrimethoxysilane, phenyltrimethoxysilane, hexamethyldisilane, methoxytrimethylsilane, triethylethoxysilane, trimethylchlorosilane, vinyltriethoxysilane and dimethyldiethoxysilane. Particularly, the alkylsilane may be at least one selected from the group consisting of methyltrimethoxysilane, ethyltrimethoxysilane, propyltrimethoxysilane and phenyltrimethoxysilane.

The solvent for the alkylsilane solution is not particularly limited as long as it is an organic solvent, and may be selected from the group consisting of methanol, dimethylformamide and a mixture (methanol/dimethylformamide) thereof.

In addition, the alkylsilane solution may have a concentration of 3-30 vol %, particularly 5-20 vol %, and more particularly 15-20 vol %. When the alkylsilane solution has a concentration less than 3 vol %, it shows hydrophilic property. The alkylsilane solution shows a continuous increase in hydrophobicity up to 30 vol %. However, when the concentration exceeds 30 vol %, there is no significant effect upon improvement in hydrophobicity despite the use of such an expensive alkylsilane solution.

The alkylsilane solution may be maintained at a temperature of 25-80° C., particularly 25-70° C., and more particularly 50-70° C. When the temperature is lower than 25° C., it is not possible to realize hydrophobicity within a predetermined time. On the other hand, a temperature higher than 80° C. is not applicable to a dipping process, since it is similar to the boiling point of the dipping solution.

The alkylsilane may be dipped in the alkylsilane solution for a dipping time of 6-48 hours, particularly 24-48 hours. When the dipping time is less than 6 hours, it is not possible to realize hydrophobicity. On the other hand, when the dipping time is more than 48 hours, it is not possible to obtain any significant improvement in hydrophobicity with time.

Dipping of the monolithic wet silica gel into the alkylsilane solution may be carried out in a batchwise or continuous mode, but is not limited thereto.

When the monolithic wet silica gel is dipped and hydrophobitized in the alkylsilane solution in which an alkylsilane compound with a structure of $R_x$—Si—$(OR)_{(4-x)}$ (wherein R is an alkyl group) is dissolved, Si—OH groups present on the surface of the wet gel and —OR groups of the alkylsilane compound are condensed to form Si—O—Si($R_x(OR)_{(3-x)}$). Finally, Si—O—Si—R structure is formed on the surface of the monolithic wet silica gel. Therefore, —R groups are substituted on the silica surface, thereby realizing hydrophobic property. In this manner, the surface and inner part of the wet silica gel are hydrophobitized.

In the method, the process of preparing wet silica gel is separated from the process of hydrophobitizing using a dipping process. When both processes are carried out simultaneously, it is not possible to obtain a desired effect as demonstrated by the following Test Example 1.

Then, the hydrophobitized monolithic wet silica gel is subjected to supercritical drying to obtain finished hydrophobic monolithic silica aerogel.

The obtained hydrophobic monolithic silica aerogel may be used in the form of hydrophobic silica aerogel powder after pulverization.

In brief, the hydrophobic monolithic silica aerogel disclosed herein is obtained by imparting hydrophobic property to monolithic wet silica gel by dipping it into an alkylsilane solution diluted with an organic solvent. FIG. 1 is a schematic view illustrating the method disclosed herein.

In addition, the method disclosed herein allows partial or total hydrophobitization of the surface of monolithic silica aerogel by using a dipping process. Thus, it is possible to control a degree of hydrophobitization of monolithic silica aerogel.

The hydrophobic monolithic silica aerogel obtained by the method disclosed herein is cost efficient by virtue of a simple and economical process, and has excellent heat insulating property and hydrophobic property so that it may be used in various industrial fields, including heat insulating panels.

The examples and experiments will now be described. The following examples and experiments are for illustrative purposes only and not intended to limit the scope of the present disclosure.

Example 1

Hydrophobic Monolithic Silica Aerogel Using Dipping Process

Tetraethoxysilane precursor is diluted with methanol and dimethylformamide as solvents in a molar ratio of 1:6:4, and then 4 moles of water and 0.005 moles of aqueous ammonia are introduced thereto to carry out hydrolysis for 2 hours. Then, gelation is carried out by using ammonium fluoride catalyst to obtain monolithic wet gel, which, in turn, is aged for 24 hours. In a separate container, methyltrimethoxysilane is diluted with methanol to provide about 3 L of solution with a concentration of 10 wt %. Then, the wet gel is introduced to the solution to perform surface hydrophobitization while maintaining room temperature (25° C.) for 24 hours. The treated wet gel is subjected to carbon dioxide substitution and supercritical drying to obtain finished monolithic silica aerogel.

Comparative Example 1

Hydrophilic Monolithic Silica Aerogel

Example 1 is repeated except that the hydrophobitization using a dipping process is omitted. As a result, hydrophilic monolithic silica aerogel is obtained.

The hydrophilic monolithic silica aerogel is determined for shrinkage, water contact angle and heat conductivity. The results are shown in the following Table 1.

Comparative Example 2

Hydrophobic Monolithic Silica Aerogel Using Co-Precursor Process

Example 1 is repeated, except that a co-precursor process in which 0.6 moles of methyltrimethoxysilane is introduced during the preparation of wet gel so that the preparation of wet silica gel is carried out simultaneously with the hydrophobitization using a dipping process. As a result, hydrophobic monolithic silica aerogel is obtained.

Test Example 1

Each monolithic silica aerogel obtained according to Example 1 and Comparative Examples 1 and 2 is determined for shrinkage, and water contact angle of each aerogel is also measured to determine hydrophobic property. In addition, to measure the heat conductivity of each monolithic silica aerogel according to Example 1 and Comparative Examples 1 and 2, a heat flow meter is used. Herein, a heat flow meter (Model: HFM 436/3/1 Lambda) available from Netzsch Co. is used to measure heat conductivity. The instrument is based on standard methods defined by ISO 8301 and ASTM C518, and is operated at 0.005-0.5 W/m·K. The instrument is used to measure the heat conductivity of the hydrophobic monolithic silica aerogel obtained as described above.

The results are shown in Table 1. Table 1 shows the shrinkage, water contact angle and heat conductivity of each monolithic silica aerogel according to Example 1 and Comparative Examples 1 and 2.

TABLE 1

| | Shrinkage (%) | Water contact angle (°) | Heat conductivity (W/m · K) |
|---|---|---|---|
| Ex. 1 | 24.2 | 121 | 0.0131 |
| Comp. Ex. 1 | 50.1 | 0 | 0.0137 |
| Comp. Ex. 2 | 54.6 | 99 | 0.0171 |

As can be seen from Table 1, the monolithic silica aerogel (Example 1) hydrophobitized by using a dipping process has low shrinkage, large water contact angle and low heat conductivity.

Example 2

Hydrophobic Monolithic Silica Aerogel with Different Dipping Solution Concentration Monolithic silica aerogel is hydrophobitized by using a dipping process in the same manner as described in Example 1, except that four methyltrimethoxysilane solutions having different concentrations (5, 10, 15, 20 wt %) are used for the dipping process.

Each hydrophobic monolithic silica aerogel obtained in this Example is determined for shrinkage, water contact angle and heat conductivity. The following Table 2 shows the shrinkage, water contact angle and heat conductivity of monolithic silica aerogel hydrophobitized with dipping solutions having a concentration of 5, 10, 15 and 20 wt %.

TABLE 2

| Dipping solution concentration (%) | Shrinkage (%) | Water contact angle (°) | Heat conductivity (W/m · K) |
| --- | --- | --- | --- |
| 5 | 24.7 | 108 | 0.0126 |
| 10 | 24.2 | 121 | 0.0128 |
| 15 | 24.0 | 130 | 0.0131 |
| 20 | 24.2 | 136 | 0.0125 |

As shown in Table 2, the monolithic silica aerogel hydrophobitized with a varied concentration of dipping solution maintains low shrinkage and heat conductivity, and shows an increase in water contact angle as the concentration of dipping solution increases.

Example 3

Monolithic silica aerogel is hydrophobitized by using a dipping process in the same manner as described in Example 1, except that temperature of a 10 wt % methyltrimethoxysilane/methanol dipping solution is varied to 25° C. and 70° C. and dipping time is varied to 6 hours and 24 hours.

Each hydrophobic monolithic silica aerogel obtained in this Example is determined for shrinkage, water contact angle and heat conductivity. The following Table 3 shows the shrinkage, water contact angle and heat conductivity of monolithic silica aerogel hydrophobitized by using a dipping solution with a temperature of 25° C. and 70° C. for a dipping time of 6 hours and 24 hours.

TABLE 3

| Dipping solution temperature (° C.) | Dipping time (h) | Shrinkage (%) | Water contact angle (°) | Heat conductivity (W/m · K) |
| --- | --- | --- | --- | --- |
| RT(25) | 24 | 24.2 | 121 | 0.0128 |
| RT(25) | 6 | 24.4 | 0 | 0.0128 |
| 70 | 6 | 18.7 | 123 | 0.0125 |
| 70 | 24 | 20.8 | 134 | 0.0133 |

As can be seen from Table 3, the monolithic silica aerogel hydrophobitized with a varied temperature of dipping solution shows a drop in shrinkage and an increase in water contact angle as the temperature increases to 70° C., and maintains low heat conductivity. In addition, when the dipping process is carried out at a temperature of 70° C. for 6 hours, the silica aerogel has decreased shrinkage and increased water contact angle as compared to the silica aerogel hydrophobitized at room temperature for 24 hours. Therefore, it can be seen that monolithic silica aerogel is hydrophobitized in a shorter time at a higher temperature of dipping solution.

Example 4

Monolithic silica aerogel is hydrophobitized by using a dipping process in the same manner as described in Example 1, except that 10 wt % methyltrimethoxysilane/methanol dipping solution is used for a dipping time of 6-48 hours (6, 12, 24, 48 hours).

Each hydrophobic monolithic silica aerogel obtained in this Example is determined for shrinkage, water contact angle and heat conductivity. The following Table 4 shows the shrinkage, water contact angle and heat conductivity of monolithic silica aerogel hydrophobitized by using a dipping solution for 6-48 hours (6, 12, 24, 48 hours).

TABLE 4

| Dipping time (h) | Shrinkage (%) | Water contact angle (°) | Heat conductivity (W/m · K) |
| --- | --- | --- | --- |
| 6 | 24.4 | 0 | 0.0128 |
| 12 | 22.3 | 103 | 0.0136 |
| 24 | 24.2 | 121 | 0.0128 |
| 48 | 22.6 | 139 | 0.0132 |

As can be seen from Table 4, the monolithic silica aerogel hydrophobitized with variable dipping times shows an increase in water contact angle as the dipping time increases, and maintains low shrinkage and heat conductivity.

Example 5

Monolithic silica aerogel is hydrophobitized by using a dipping process in the same manner as described in Example 1, except that different alkylsilane solutions are used. The alkylsilane solutions used in this Example include methyltrimethoxysilane, ethyltrimethoxysilane, propyltrimethoxysilane and phenyltrimethoxysilane solutions.

Each hydrophobic monolithic silica aerogel obtained in this Example is determined for shrinkage, water contact angle and heat conductivity. The following Table 5 shows the shrinkage, water contact angle and heat conductivity of monolithic silica aerogel hydrophobitized by using different dipping solutions.

TABLE 5

| Dipping solution | Shrinkage (%) | Water contact angle (°) | Heat conductivity (W/m · K) |
| --- | --- | --- | --- |
| Methyltrimethoxysilane | 24.2 | 121 | 0.0128 |
| Ethyltrimethoxysilane | 33.0 | 122 | 0.0127 |
| Propyltrimethoxysilane | 34.2 | 133 | 0.0131 |
| Phenyltrimethoxysilane | 38.3 | 132 | 0.0137 |

As can be seen from Table 5, when the monolithic silica aerogel is hydrophobitized by using different dipping solutions, methyltrimethoxysilane provides the lowest shrinkage and water contact angle, and propyltrimethoxysilane provides the highest water contact angle, and thus high hydrophobic property. Even when different dipping solutions are used, low heat conductivity is still maintained.

Example 6

Monolithic silica aerogel is hydrophobitized by using a dipping process in the same manner as described in Example 1, except that different solvents for a dipping solution are used. The solvents used in this Example include methanol, dimethylformamide and a mixed solvent of methanol/dimethylformamide (molar ratio=6/4).

Each hydrophobic monolithic silica aerogel obtained in this Example is determined for shrinkage, water contact angle and heat conductivity. The following Table 6 shows the shrinkage, water contact angle and heat conductivity of monolithic silica aerogel hydrophobitized by using different solvents for a dipping solution.

TABLE 6

| Dipping solution | Shrinkage (%) | Water contact angle (°) | Heat conductivity (W/m · K) |
|---|---|---|---|
| Methanol | 24.2 | 121 | 0.0128 |
| Methanol/dimethylformamide | 20.8 | 126 | 0.0124 |
| Dimethylformamide | 18.3 | 133 | 0.0124 |

As can be seen from Table 6, when the monolithic silica aerogel is hydrophobitized by using different solvents for a dipping solution, dimethylformamide causes a decrease in shrinkage and an increase in water contact angle. Even when different solvents are used, low heat conductivity is still maintained.

What is claimed is:

1. A method for preparing hydrophobic monolithic silica aerogel, comprising:
   preparing monolithic wet silica gel by using an alkoxide precursor and introducing the wet silica gel to a monolithic mould thereby carrying out gelation to prepare a monolithic wet silica gel;
   controlling a degree of hydrophobization of the monolithic wet silica gel by dipping the wet gel into an alkylsilane solution through a dipping process; and
   carrying out supercritical drying of the hydrophobitized monolithic wet silica gel,
   wherein the alkylsilane solution is maintained at a temperature of 50-70° C. and the monolithic wet silica gel is dipped in the alkylsilane solution for 6-48 hours, and
   wherein the alkylsilane solution has a concentration of 5-20 vol %.

2. The method for preparing hydrophobic monolithic silica aerogel according to claim 1, wherein the alkylsilane is at least one selected from the group consisting of methyltrimethoxysilane, ethyltrimethoxysilane, propyltrimethoxysilane, phenyltrimethoxysilane, hexamethyldisilane, methoxytrimethylsilane, triethylethoxysilane, trimethylchlorosilane, vinyltriethoxysilane and dimethyldiethoxysilane.

3. The method for preparing hydrophobic monolithic silica aerogel according to claim 1, wherein the solvent used for the alkylsilane solution is selected from the group consisting of methanol, dimethylformamide and a mixture thereof.

4. The method for preparing hydrophobic monolithic silica aerogel according to claim 1, wherein said hydrophobitization is carried out in a batchwise or continuous mode.

* * * * *